(12) United States Patent
King

(10) Patent No.: US 8,389,064 B2
(45) Date of Patent: Mar. 5, 2013

(54) SYSTEM AND METHOD FOR PROTECTING ENCLOSURE FROM SOLAR RADIATION

(75) Inventor: John D. H. King, Santa Monica, CA (US)

(73) Assignee: Combined Power, LLC, Santee, CA (US)

( * ) Notice: Subject to any disclaimer, the term of this patent is extended or adjusted under 35 U.S.C. 154(b) by 1120 days.

(21) Appl. No.: 12/253,962

(22) Filed: Oct. 18, 2008

(65) Prior Publication Data

US 2010/0095583 A1 Apr. 22, 2010

(51) Int. Cl.
| | |
|---|---|
| *B05D 1/02* | (2006.01) |
| *B05D 5/00* | (2006.01) |
| *B05D 7/00* | (2006.01) |
| *B28B 19/00* | (2006.01) |
| *B29B 15/10* | (2006.01) |
| *C23C 18/00* | (2006.01) |
| *C23C 20/00* | (2006.01) |
| *C23C 28/00* | (2006.01) |

(52) U.S. Cl. ............... 427/427.3; 435/289.1; 435/292.1; 435/298.1; 239/159; 47/17

(58) Field of Classification Search ............... 427/427.1; 47/17
See application file for complete search history.

(56) References Cited

U.S. PATENT DOCUMENTS

| | | | | |
|---|---|---|---|---|
| 3,107,055 | A * | 10/1963 | Palmer | 239/164 |
| 3,914,469 | A * | 10/1975 | Delano et al. | 427/164 |
| 4,895,904 | A | 1/1990 | Allingham | |
| 5,383,599 | A * | 1/1995 | Zur | 239/77 |
| 5,522,544 | A * | 6/1996 | Gal | 239/78 |
| 5,771,630 | A | 6/1998 | Harasawa et al. | |
| 5,939,089 | A | 8/1999 | Wirtz et al. | |
| 6,282,834 | B1 * | 9/2001 | Mossey | 47/17 |
| 6,350,521 | B1 | 2/2002 | Chen et al. | |
| 6,436,377 | B1 | 8/2002 | Hansenne et al. | |
| 6,892,743 | B2 * | 5/2005 | Armstrong et al. | 135/143 |
| 6,974,850 | B2 | 12/2005 | McMan et al. | |
| 2008/0178739 | A1 * | 7/2008 | Lewnard et al. | 95/186 |

OTHER PUBLICATIONS

Zhang et al., UV-Blocking Properties of Silica/Titania Hybrid Nanocomposites, Key Engineering Materials vols. 334-335 pp. 1065-1068 (Mar. 2007).*
Yang et al., Studying the Mechanisms of Titanium Dioxide as Ultraviolet-Blocking Additive for Films and Fabrics by an Improved Scheme, Journal of Applied Polymer Science, vol. 92, pp. 3201-3210 (2004).*
Press release, "Purfresh Introduces Crop Yield Enhancement for Solar and Water Stress," Jul. 29, 2008.

* cited by examiner

*Primary Examiner* — Timothy Meeks
*Assistant Examiner* — Michael P Rodriguez
(74) *Attorney, Agent, or Firm* — Tsircou Law, P.C.

(57) ABSTRACT

A system and method are provided for protecting bio-reactor housing from solar radiation, by applying UV-protective material to an outer surface of a plastic wall of the bio-reactor housing to protect from solar radiation. The housing includes a wall formed of plastic that defines the outer surface. In this manner, the effective life of the housing is extended and the overall cost of generation of photosynthetic biomass is decreased, improving system performance and cost-effectiveness.

20 Claims, 3 Drawing Sheets

US 8,389,064 B2

SYSTEM AND METHOD FOR PROTECTING ENCLOSURE FROM SOLAR RADIATION

FIELD OF THE INVENTION

The present invention relates generally to enclosures for growing photosynthetic organisms and, more particularly, to protecting such enclosures from solar radiation.

BACKGROUND OF THE INVENTION

The production of algal biomass has increasingly been of interest. The potential usage of such material is found across a wide range of applications, including biofuel feedstock production, fertilizer, nutritional supplements, pollution control, and other uses.

For example, various approaches such as "open-air" and "closed-air," have been considered for mass production of algal biomass. The United States Department of Energy conducted a program called the Aquatic Species Program from 1978 to 1996. The engineering efforts of the program were largely focused on large "open-air" racetrack pond designs. The ponds are so-named based on the fact that the culture medium is conveyed in a complete circuit in a continuous fashion. This flow of culture medium is achieved with large continuously turning paddle wheels, which induce a turbulent flow in the medium. The turbulent flow is necessary to mix the culture so that all algae cells receive sunlight. The ponds are similar in appearance to extremely elongated ovals.

Although such "open-air" approaches are generally effective, shortfalls exist. For example, such systems risk incursion of invasive species, which can severely hamper growth of the desired algae. Evaporation of culture medium leading to large demands on water resources is a significant issue. In addition, such open-air approaches are not as effective as closed systems in sequestration of carbon dioxide emissions.

"Closed-air" systems generally refer to systems that contain algal biomass production within a controlled environment, limiting exposure to outside air. Examples of such systems include closed photo-bioreactor structures forming a closed container for housing a culture medium for generating algal biomass. Having a controlled environment helps maximize the generation of algal material by limiting exposure to invasive species as well as controlling other environmental factors that promote algal growth. Closed-air systems significantly reduce evaporation and therefore significantly reduce demands on water resources. In addition, closed-air systems facilitate the sequestration of carbon dioxide gas, which promotes algal growth, facilities compliance with environmental regulations, and benefits the environment generally.

Accordingly, such closed-air systems are beneficial in many respects. However, such systems can be expensive and, in many instances, cost prohibitive. One of the main areas of cost for algal photo-bioreactors is the reactor material itself. Clear glass or acrylic tubes cost so much that the economic value of the biomass generated within the reactor over its lifetime may not be high enough to pay for the reactor itself.

Lightweight plastic film has been used as an alternative structure for providing a container for housing a culture medium. Such plastic film structures are comparatively inexpensive to set up, however, such material is much more prone to degradation, particularly from extended exposure to solar radiation. Current implementations that use such materials typically result in an effective useful lifetime between about one to two years. Thus, considering such a short lifespan, cost effectiveness of such structures is questionable.

It should be appreciated that there remains a need for a system and method of generating algal biomass in an efficient and cost-effective manner. The present invention fulfills this need and others.

SUMMARY OF THE INVENTION

In general terms, the present invention provides a system and method for protecting bio-reactor housing from solar radiation, by applying UV-protective material to an outer surface of a plastic wall of the bio-reactor housing to protect it from solar radiation. The housing includes a wall formed of plastic that defines the outer surface. In this manner, the effective life of the housing is extended and the overall generation of algal biomass is increased, improving system performance and cost-effectiveness.

More particularly, by example only and not limitation, the housing can be formed of an elongated plastic tube configured to house a culture medium for generating algal biomass. The tubes can be formed of plastic comprised of polyethylene.

In an exemplary embodiment in accordance with the invention, a system for generating algal biomass includes a plurality of elongated plastic tubes that house a culture medium for generating algal biomass. The plastic tubes positioned such that the tubes are exposed to solar radiation. A film of UV-protective material disposed on an outer surface of the plastic tubes. The system further includes a spray system for applying UV protective material onto the plastic tubes. The spray system including a tank containing a liquid comprising UV-protective material and a plurality of nozzles configured to dispense the UV-protective material onto the outer surface of the plastic tubes.

In a detailed aspect of an exemplary embodiment, the UV-protective material includes a UV-blocking compound selected from a group consisting of octisalate, zinc oxide, ecamsule, titanium dioxide, homosalate, octocrylene, oxybenzone, and avobenzone.

In another detailed aspect of an exemplary embodiment, the outer surface of the housing is provided with a film of UV-protective material having a thickness between about 1 and 40 microns.

In yet another detailed aspect of an exemplary embodiment, the spray system can further be mounted on a vehicle such that a boom of the spray system extends over the housing. The elongated plastic tubes are aligned with each other in a manner to allow the vehicle to pass along side the plastic tubes such that the boom of the spray system extends over the plastic tubes.

In yet another detailed aspect of an exemplary embodiment, the plastic tubes are disposed in at least one pool of liquid to support the plastic tubes.

For purposes of summarizing the invention and the advantages achieved over the prior art, certain advantages of the invention have been described herein. Of course, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which.

DETAILED DESCRIPTION OF EXEMPLARY EMBODIMENTS

Figure 1:
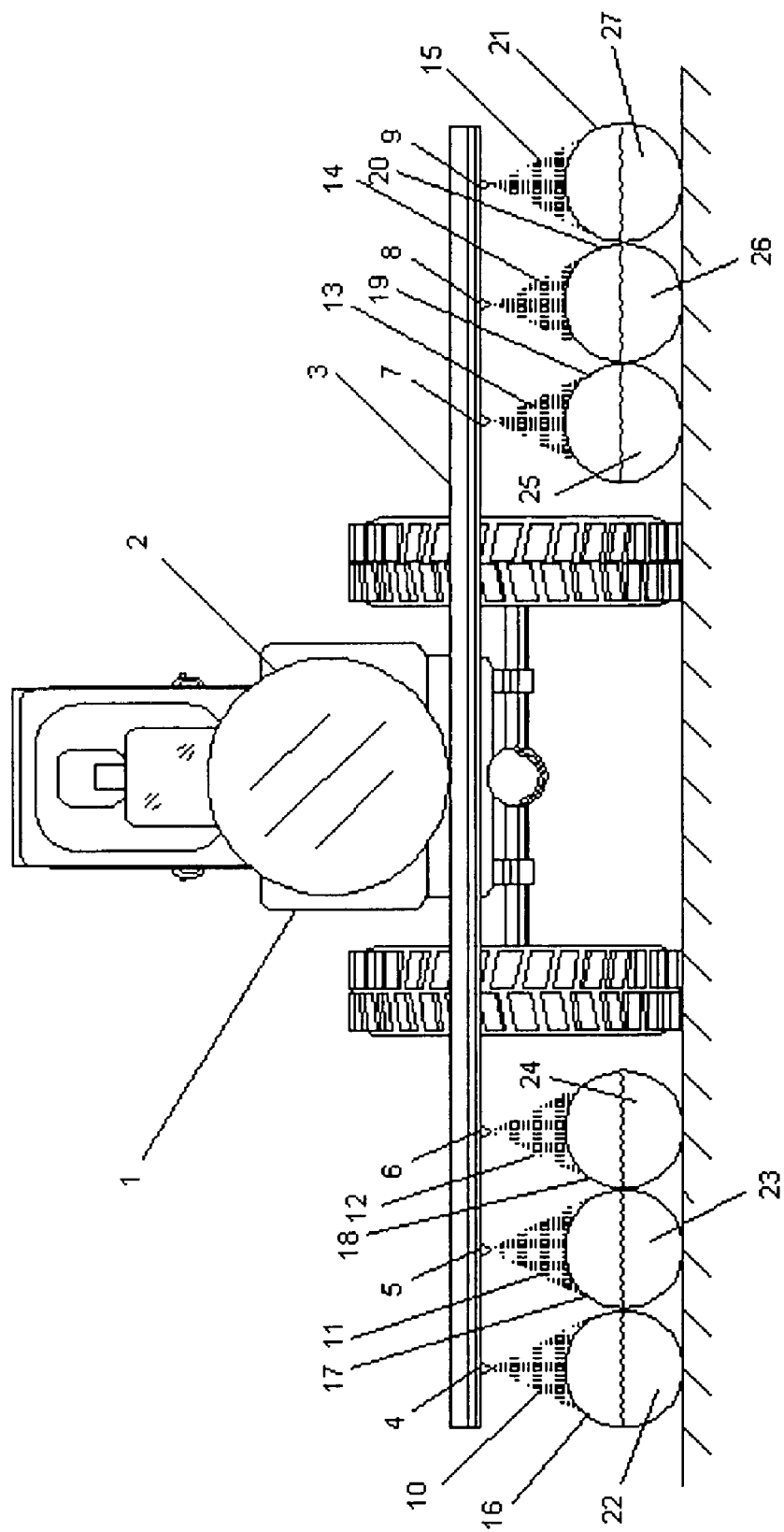
FIG. 1 is an elevational view of a tractor configured to apply UV protection onto photo-bioreactor enclosures in accordance with a first embodiment of the present invention.

With reference now to the drawings, and particularly FIG. 1, there is shown an agricultural tractor 1 mounted with a spray system for applying UV protective film on to photo-bioreactor tubes. More particularly, the tractor is shown maneuvering between two arrays of tubes (16-21) containing algae culture medium (22-27) and disposed horizontally along the ground. The spray system is used to provide a UV-protective film applied directly to the outer surface of a plastic substrate of the tube to protect the tubes and the algae culture medium from harmful UV radiation. In this manner, the effective life of the photo-bioreactor tubes is extended and the overall generation of algal biomass is increased, improving system performance and cost-effectiveness.

The spray system for the tractor 1 includes a tank 2 that houses a UV-protective compound containing agents such as, e.g., octisalate, homosalte, or avobenzone. UV-protective materials are selected to provide protection from the portion of the UV range of the spectrum that is most damaging to the target plastic substrate. In the exemplary embodiment, the tubes (16-21) are formed of polyethylene, which can be particularly susceptible to solar radiation within the UV-B range. Thus, UV-protective materials are selected to ensure protection within the UV-B range.

The tank is coupled to a boom 3 sized to extend over the photo-bioreactor tubes (16-21). The boom includes a plurality of nozzles (4-9) positioned to be aligned above the tubes (16-21), when in use. In the exemplary embodiment, the nozzles are positioned between about 10 cm and 30 cm above the tubes.

The tubes (16-21) are formed of polyethylene, configured in an elongated cylindrical configuration, which is maintained by positive pressure within the tube. The tubes are configured to be at least partially filled with an algae culture medium. The level of liquid within the tube can vary, from empty to fully filled with liquid, though in normal use it is desirable to maintain the tubes at about half full such that the liquid surface extends across the diameter of the tube's cross section to maximize surface area exposure.

In the exemplary embodiment, the tubes are formed of a single sheet of plastic, having a thickness between about 4 mil and 10 mil. In other embodiments, tubes can be formed of multiple layers of material. The UV-protective material is preferably applied to the outer surface of the tubes. Tubes of various sizes can be used, to include tube diameter and tube length, without departing from the invention.

The nozzles (4-9) are configured to convert the UV-protective compound to an aerosol form, such that UV-protective compound dispenses in a fine mist to provide a thin layer of UV-protective material on the tubes (16-21). In the exemplary embodiment, the spray system further includes a compressor to force material out of the nozzles. In use, the aerosol lands on the surface of the tube and dries in place. In the exemplary embodiment, UV-protective compound provides a protective film having a thickness between about 1 and 40 microns, and more preferably, between about 1 to 4 micron, per application of UV-protective compound. As a result, a small amount of UV-protective material can be used to protect the plastic tube from solar radiation, thereby maximizing its effective life. Subsequent coatings of UV-protective material can be applied in situ while the tubes are in use, producing biomass.

In the exemplary embodiment, the UV-protective material forms a protective film on the outer surface of the tubes. Chemical bonding between the UV-protective material and the plastic tubes may or may not form without departing from the invention.

Figure 2:
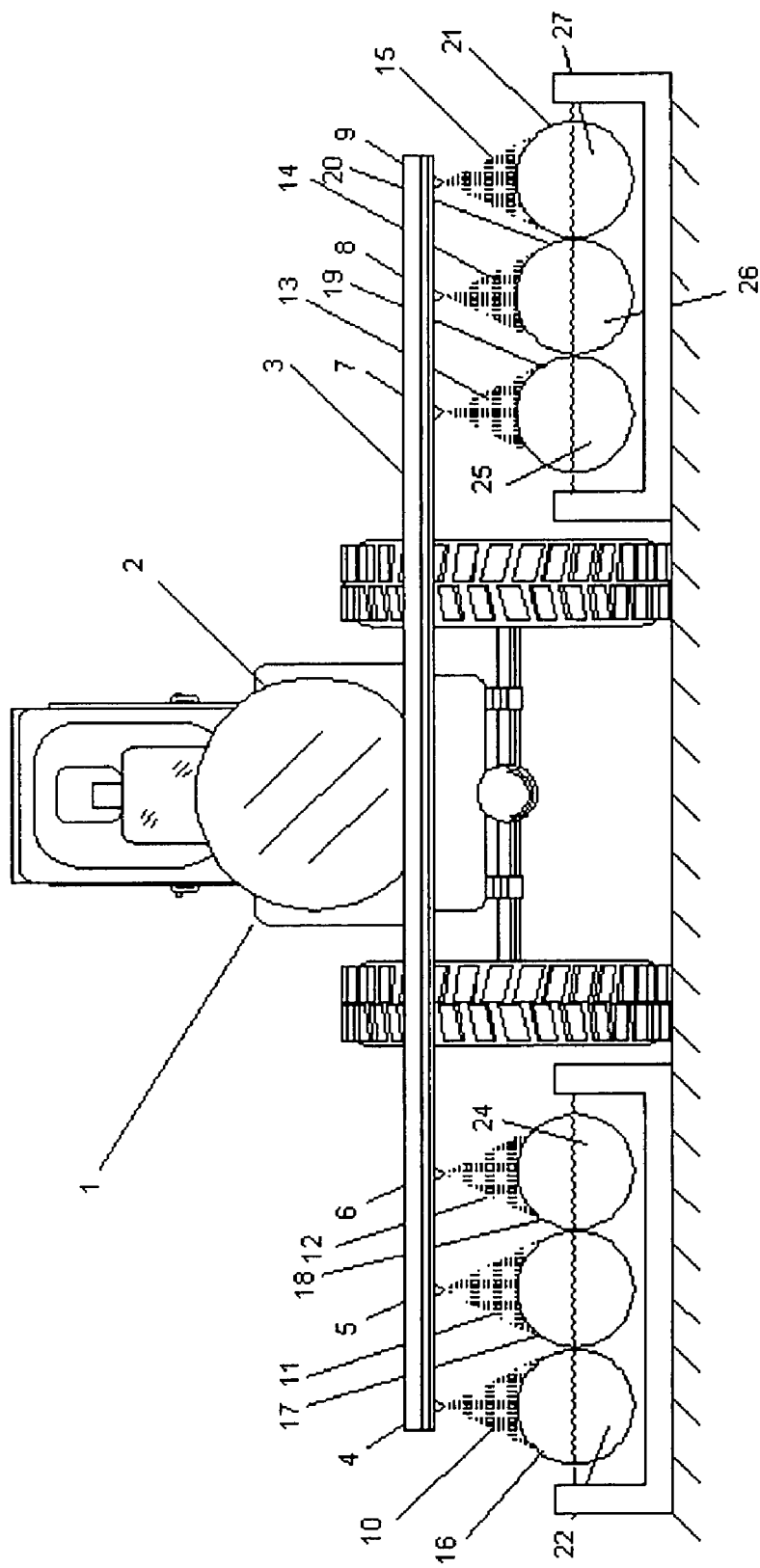
FIG. 2 is an elevational view of a tractor configured to apply UV protection onto photo-bioreactor enclosures in accordance with a second embodiment of the present invention.

With reference now to FIG. 2, the tractor 1 is shown maneuvering between two ponds with floating tubular photo-bioreactors (16-19) floating in the ponds. A chemical tank and aerosol sprayers are mounted on the tractor such that the spray nozzles (4-9) are optimally positioned with respect to vertical height and horizontal spacing in order to deposit a coating of UV-protective film on the surface of the tubes. The UV-protective film deposits and dries on the top part of the tubes in much the same way as with tubes disposed on land as in FIG. 1. The UV-protective material may or may not form a chemical bond with the plastic tubes without departing from the invention.

Figure 3:
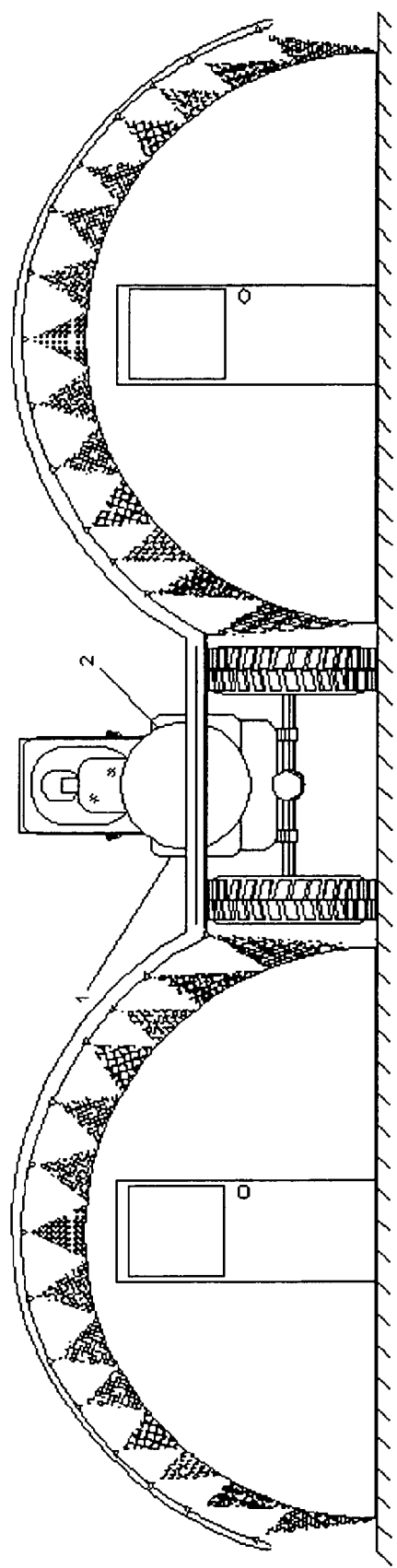
FIG. 3 is an elevational view of a tractor configured to apply UV protection onto photo-bioreactor enclosures in accordance with a third embodiment of the present invention.

With reference now to FIG. 3, a tractor 1 is shown maneuvering between two green houses having a plastic outer wall. The tractor includes a tank and two booms positioned on either side of the tractor. Spray nozzles are positioned along the length of each boom. The booms are positioned to put the spray nozzles in close physical proximity to the surface of the thin plastic greenhouse cover. The nozzles deliver a spray coating of UV-protective material, which dries in place providing UV blocking benefits to the greenhouses. Multiple coatings can be used during the lifetime of the plastic greenhouse cover. The greenhouse can be utilized for generating any sort of biological material (e.g., flora or fauna) that benefits from solar exposure.

In the exemplary embodiments, a tractor having a spray system is used to apply the UV-protective material. Nonetheless, any other embodiment can utilize various other methods for dispensing UV-protective material onto the outer surface of the plastic material without departing from the invention. For example, various sprinkler systems, aircraft having spray systems, backpack mounted tank with a handheld sprayer, as well as various other means known in the art can be used. Moreover, the invention has been discussed with regard to selected enclosure configurations; however, other enclosures can be used, particularly those having an outer plastic surface, without departing from the invention.

Although the invention has been disclosed in detail with reference only to the exemplary embodiments, those skilled in the art will appreciate that various other embodiments can be provided without departing from the scope of the invention. Accordingly, the invention is defined only by the claims set forth below.

What is claimed is:

1. A method of protecting plastic housings from solar radiation, comprising:

providing a vehicle having a tank and a plurality of booms, the tank containing a liquid comprising UV-protective material, the booms having a plurality of nozzles for dispensing the UV-protective material;

transporting the vehicle between two arrays of elongated housings aligned in parallel on opposing sides of the vehicle such that the booms are disposed above the arrays of elongated housings, each of the housings is formed of a single sheet of plastic having a thickness about 4 mil and 10 mil configured in an elongated cylindrical enclosure maintained by positive pressure within the enclosure relative to exterior air pressure; and dispensing the UV-protective material from the booms onto the arrays of elongated housing as the vehicle travels between the arrays in a manner such that a film of the UV-protective material is provided along the length of each of the housings.

2. A method as defined in claim 1, wherein the dispensing step provides the film at a thickness between about 1 and 40 microns along the length of each of the housings.

3. A method as defined in claim 1, wherein each of the arrays of housings is disposed in a pool of liquid to support the housings.

4. A method as defined in claim 1, wherein the dispensing step provides the film at a thickness between about 1 and 4 microns along the length of each of the housings.

5. A method as defined in claim 1, wherein the UV-protective material includes a UV-blocking compound selected from the group consisting of octisalate, zinc oxide, ecamsule, titanium dioxide, homosalate, octocrylene, oxybenzone, and avobenzone.

6. A method as defined in claim 1, wherein the plastic comprises polyethylene.

7. A method as defined in claim 1, wherein the plurality of nozzles are aligned with the housings such that a single nozzle is centered above each housing of the arrays of housings.

8. A method of protecting plastic housings from solar radiation, comprising:

providing a vehicle having a tank and a plurality of booms, the tank containing a liquid comprising UV-protective material, the booms having a plurality of nozzles for dispensing the UV-protective material;

transporting the vehicle between two arrays of elongated housings aligned in parallel on opposing sides of the vehicle such that the booms are disposed above the arrays of elongated housings, such that each housing has a nozzle disposed above the housing, each of the housings is formed of a single sheet of plastic having a thickness about 4 mil and 10 mil configured in an elongated cylindrical enclosure maintained by positive pressure relative to exterior air pressure; and dispensing the UV-protective material from the booms onto the arrays of elongated housing as the vehicle travels between the arrays in a manner such that a film of the UV-protective material is provided along the length of each of the housings.

9. A method as defined in claim 8, wherein the dispensing step provides the film at a thickness between about 1 and 40 microns along the length of each of the housings.

10. A method as defined in claim 8, wherein each of the arrays of housings is disposed in a pool of liquid to support the housings.

11. A method as defined in claim 8, wherein the dispensing step provides a film having UV-protective material having a thickness between about 1 and 4 microns.

12. A method as defined in claim 8, wherein the UV-protective material includes a UV-blocking compound selected from the group consisting of octisalate, zinc oxide, ecamsule, titanium dioxide, homosalate, octocrylene, oxybenzone, and avobenzone.

13. A method as defined in claim 8, wherein the plastic comprises polyethylene.

14. A method as defined in claim 8, wherein the plurality of nozzles are aligned with the housings such that a single nozzle is centered above each housing.

15. A method of protecting plastic housings from solar radiation, comprising:

providing a vehicle having a tank and a plurality of booms, the tank containing a liquid comprising UV-protective material, the booms having a plurality of nozzles for dispensing the UV-protective material;

transporting the vehicle between two arrays of elongated housings aligned in parallel on opposing sides of the vehicle such that the booms are disposed above the arrays of elongated housings, each of the arrays of housings is disposed in a pool of liquid to support the housings; and dispensing the UV-protective material from the booms onto the arrays of elongated housing as the vehicle travels between the arrays in a manner such that a film of the UV-protective material is provided along the length of each of the housings.

16. A method as defined in claim 15, wherein the dispensing step provides the film at a thickness between about 1 and 40 microns along the length of each of the housings.

17. A method as defined in claim 15, wherein the dispensing step provides the film at a thickness between about 1 and 4 microns along the length of each of the housings.

18. A method as defined in claim 15, wherein the UV-protective material includes a UV-blocking compound selected from the group consisting of octisalate, zinc oxide, ecamsule, titanium dioxide, homosalate, octocrylene, oxybenzone, and avobenzone.

19. A method as defined in claim 15, wherein the plastic comprises polyethylene.

20. A method as defined in claim 15, wherein the plurality of nozzles are aligned with the housings such that each housing has a nozzle disposed above the housing.

\* \* \* \* \*